US012167938B2

(12) United States Patent
Choi

(10) Patent No.: US 12,167,938 B2
(45) Date of Patent: Dec. 17, 2024

(54) MULTIPURPOSE LASER POINTING-EQUIPMENT FOR MEDICAL USE

(71) Applicant: Hong Hee Choi, Seoul (KR)

(72) Inventor: Hong Hee Choi, Seoul (KR)

( * ) Notice: Subject to any disclaimer, the term of this patent is extended or adjusted under 35 U.S.C. 154(b) by 336 days.

(21) Appl. No.: 17/829,155

(22) Filed: May 31, 2022

(65) Prior Publication Data

US 2022/0287792 A1 Sep. 15, 2022

Related U.S. Application Data

(63) Continuation of application No. PCT/KR2020/019167, filed on Dec. 27, 2020.

(30) Foreign Application Priority Data

Jan. 8, 2020 (KR) ........................ 10-2020-0002802

(51) Int. Cl.
*A61B 90/50* (2016.01)
*A61B 17/70* (2006.01)
(Continued)

(52) U.S. Cl.
CPC .......... *A61B 90/13* (2016.02); *A61B 17/7076* (2013.01); *A61B 2090/061* (2016.02)

(58) Field of Classification Search
CPC ................................ A61B 90/50; A61B 90/13
See application file for complete search history.

(56) References Cited

U.S. PATENT DOCUMENTS 5,450,148 A * 9/1995 Shu ........................ G02B 27/20 353/42
5,606,590 A * 2/1997 Petersen ................ A61B 90/50 378/177
(Continued)

FOREIGN PATENT DOCUMENTS

JP 2006312079 A 11/2006
KR 200198708 Y1 10/2000
(Continued)

OTHER PUBLICATIONS

International search report of PCT/KR2020/019167, Apr. 9, 2021, English translation.

*Primary Examiner* — Zade Coley
(74) *Attorney, Agent, or Firm* — STIP Law Group, LLC

(57) ABSTRACT

The present disclosure relates to a multipurpose laser pointing-equipment for medical use, and more particularly to a multipurpose laser pointing-equipment for medical use that can minimize errors in an operation (treatment, surgery) by definitely marking a reference for a surgery part from the outside the patient's body using point and line types of laser beams and by making it possible to accurately measure the surgical target.

The present disclosure is characterized by including: a pointer assembly lifted from a floor and emitting downward a laser beam for marking a reference for a surgical part on the body of a patient and for measuring a surgical range; a standing base being a basis for supporting the equipment in an erect position; a positioning supporter being erect on the standing base to lift the pointer assembly and adjust a height, a position, and an angle of the pointer assembly; and a controller disposed at a position for a user to operate the equipment.

5 Claims, 13 Drawing Sheets

33
32
S
S
1
331
S
S
h
h
122'
122
121
SPOT TYPE LASER BEAM
(MARKING REFERENCE FOR
SURGICAL TARGET)
12 : 121, 122, 122'
OPERATION PROSTHESIS
OPERATION PROSTHESIS
SPINE

(51) Int. Cl.

| | |
|---|---|
| ***A61B 90/13*** | (2016.01) |
| *A61B 90/00* | (2016.01) |

(56) References Cited

U.S. PATENT DOCUMENTS

| | | | | |
|---|---|---|---|---|
| 6,368,332 | B1 * | 4/2002 | Salcudean | A61B 90/50<br>606/1 |
| 2007/0055291 | A1 * | 3/2007 | Birkmeyer | A61B 17/1671<br>606/130 |
| 2013/0060134 | A1 * | 3/2013 | Eshima | G01T 1/1614<br>600/431 |
| 2016/0000516 | A1 * | 1/2016 | Cheng | A61B 34/20<br>600/424 |
| 2016/0038238 | A1 * | 2/2016 | Kostrzewski | A61B 34/76<br>606/279 |
| 2016/0166333 | A1 * | 6/2016 | Wang | A61B 34/10<br>600/476 |

FOREIGN PATENT DOCUMENTS

| | | | |
|---|---|---|---|
| KR | 200364087 | Y1 | 10/2004 |
| KR | 20100112309 | A | 10/2010 |
| KR | 101577564 | B1 | 12/2015 |
| KR | 20190131169 | A | 11/2019 |
| KR | 102056436 | | 12/2019 |
| WO | WO2017213425 | A1 | 12/2017 |

* cited by examiner

[FIG. 1]
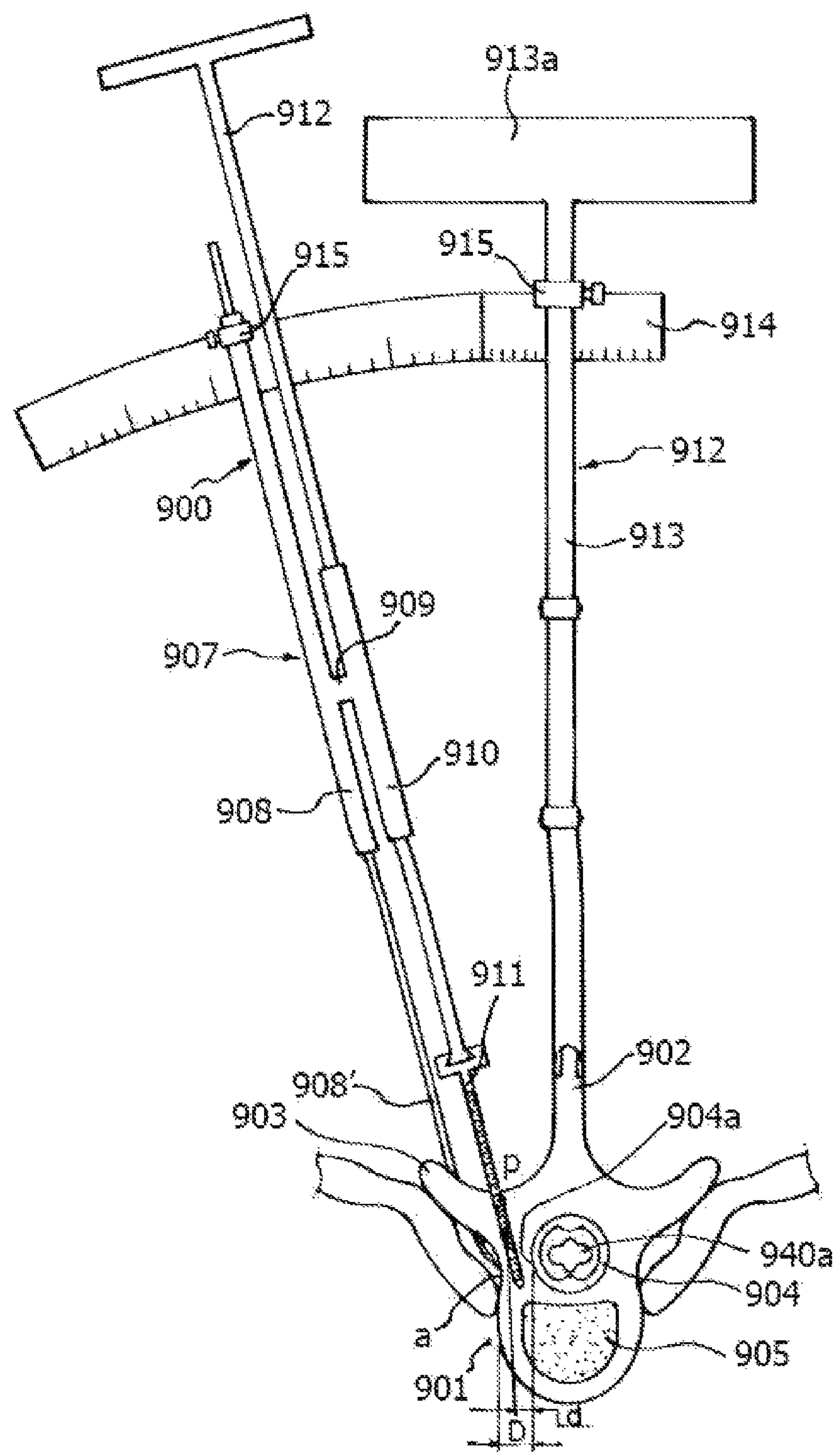

[FIG. 2]
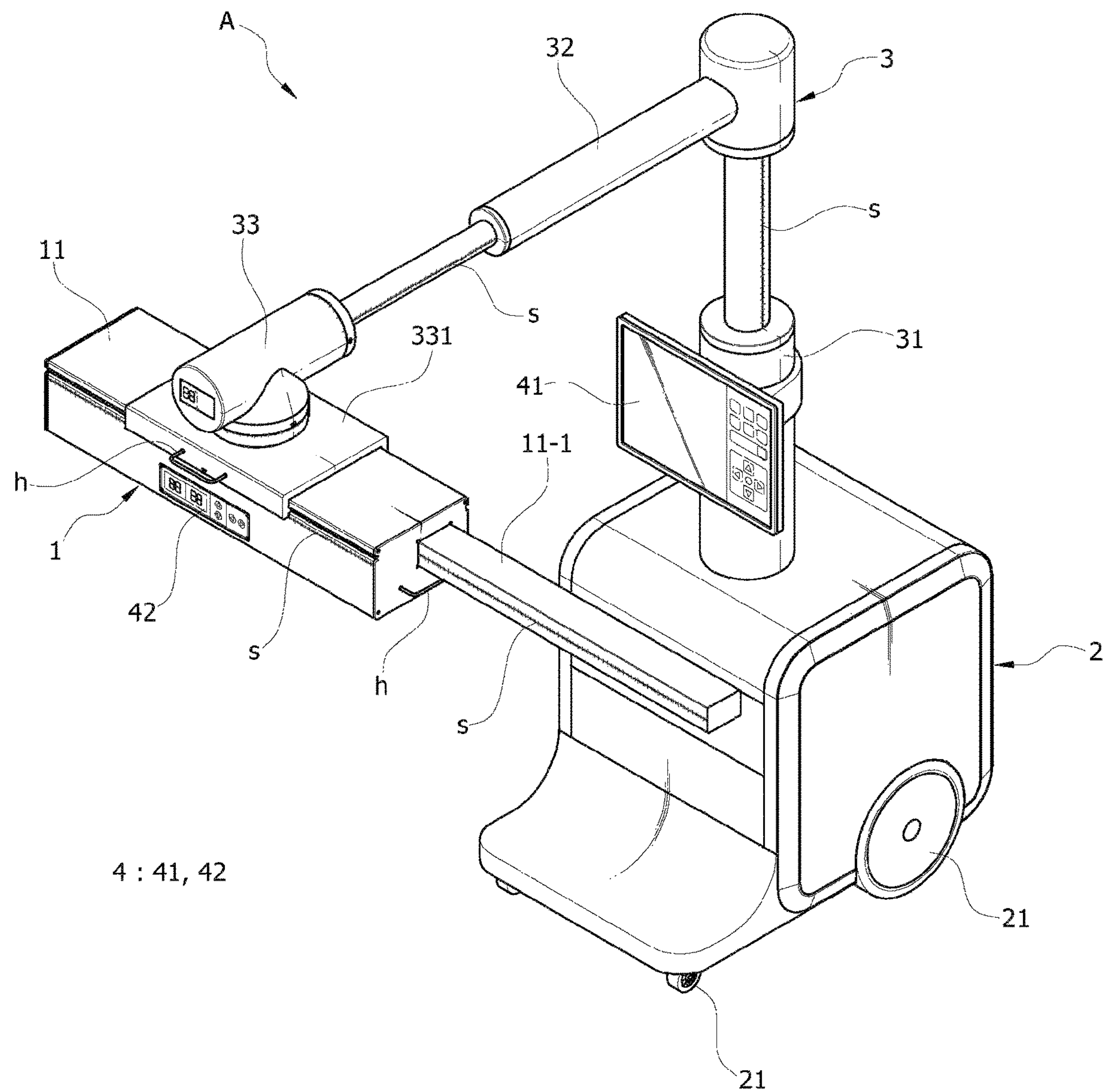

[FIG. 3(a)]
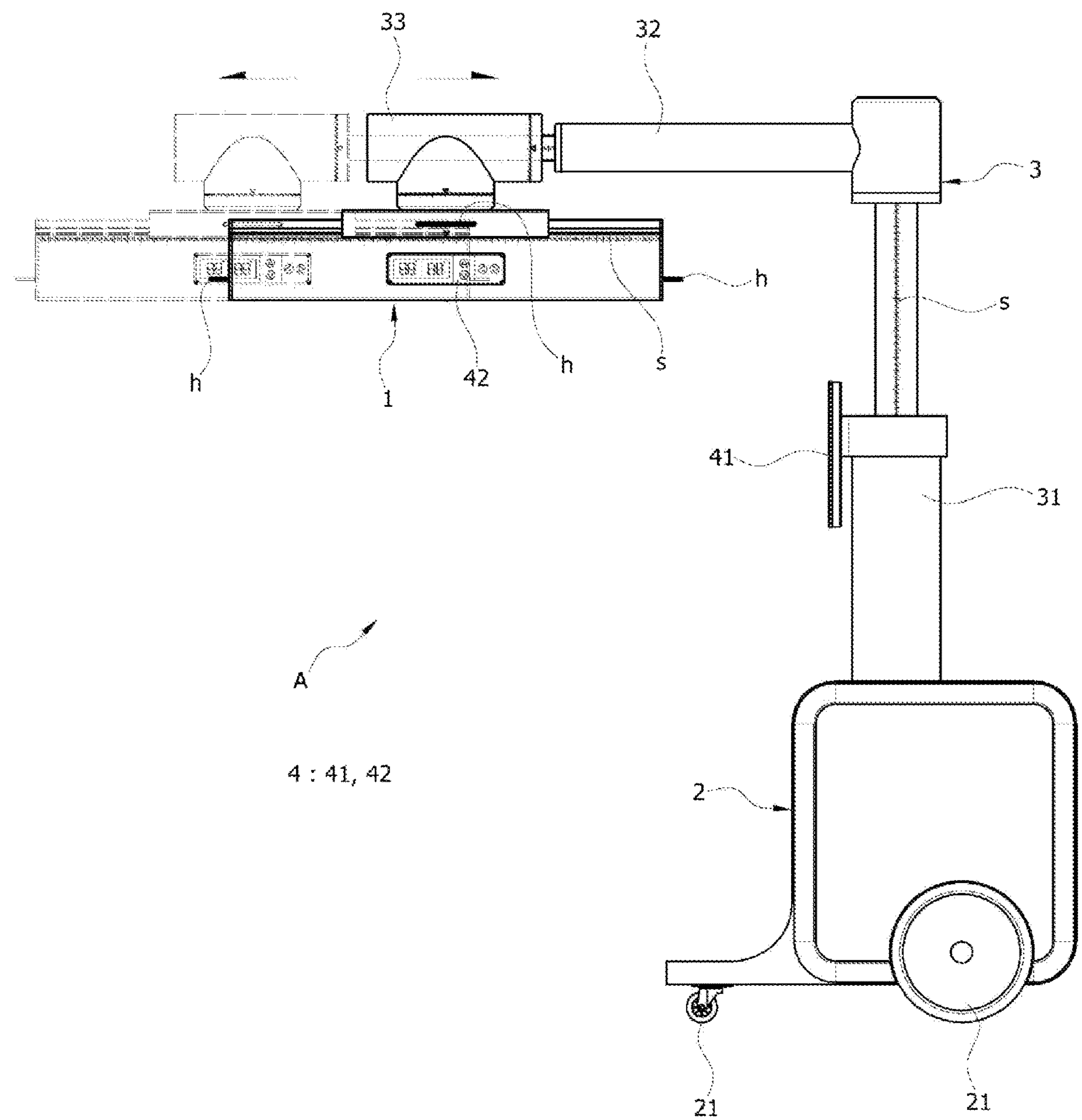

[FIG. 3(b)]
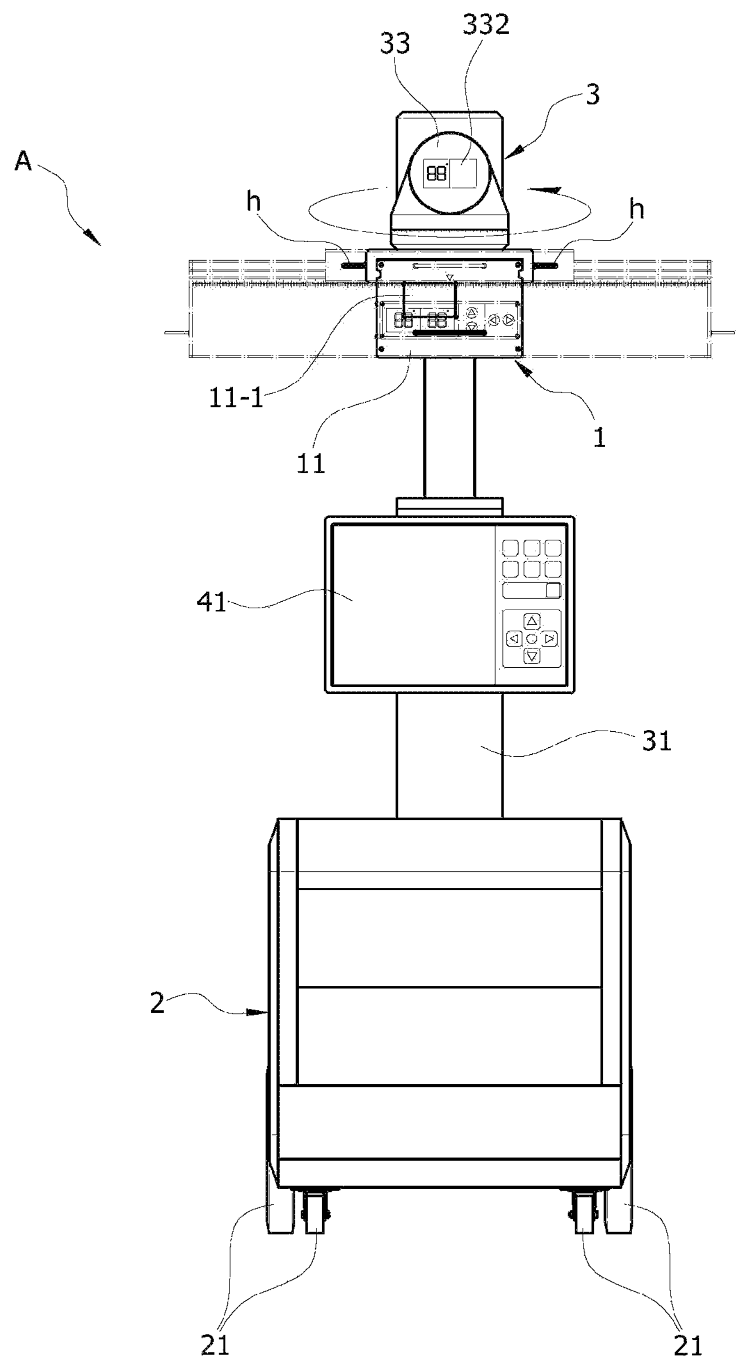

[FIG. 4]
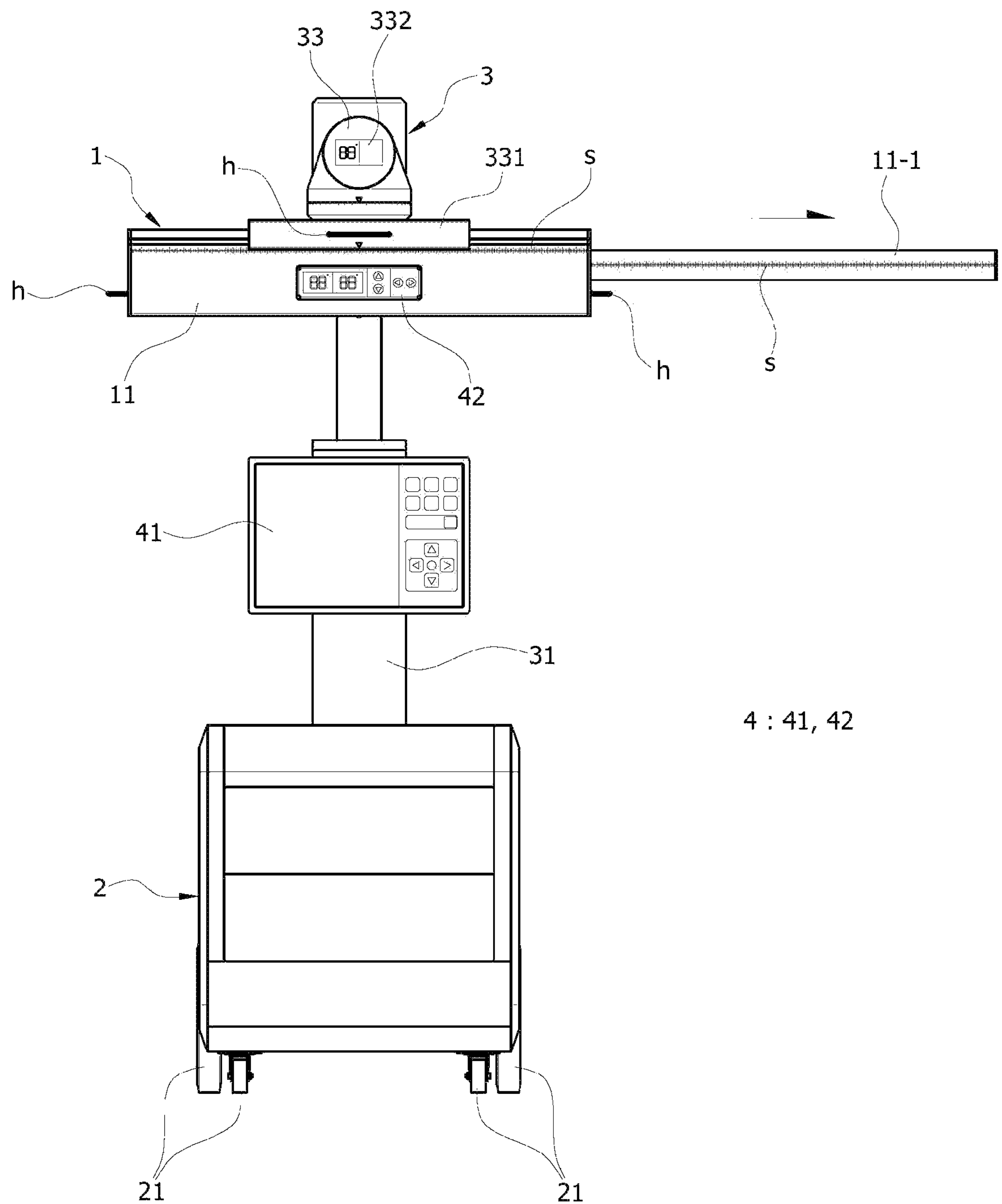

[FIG. 5]
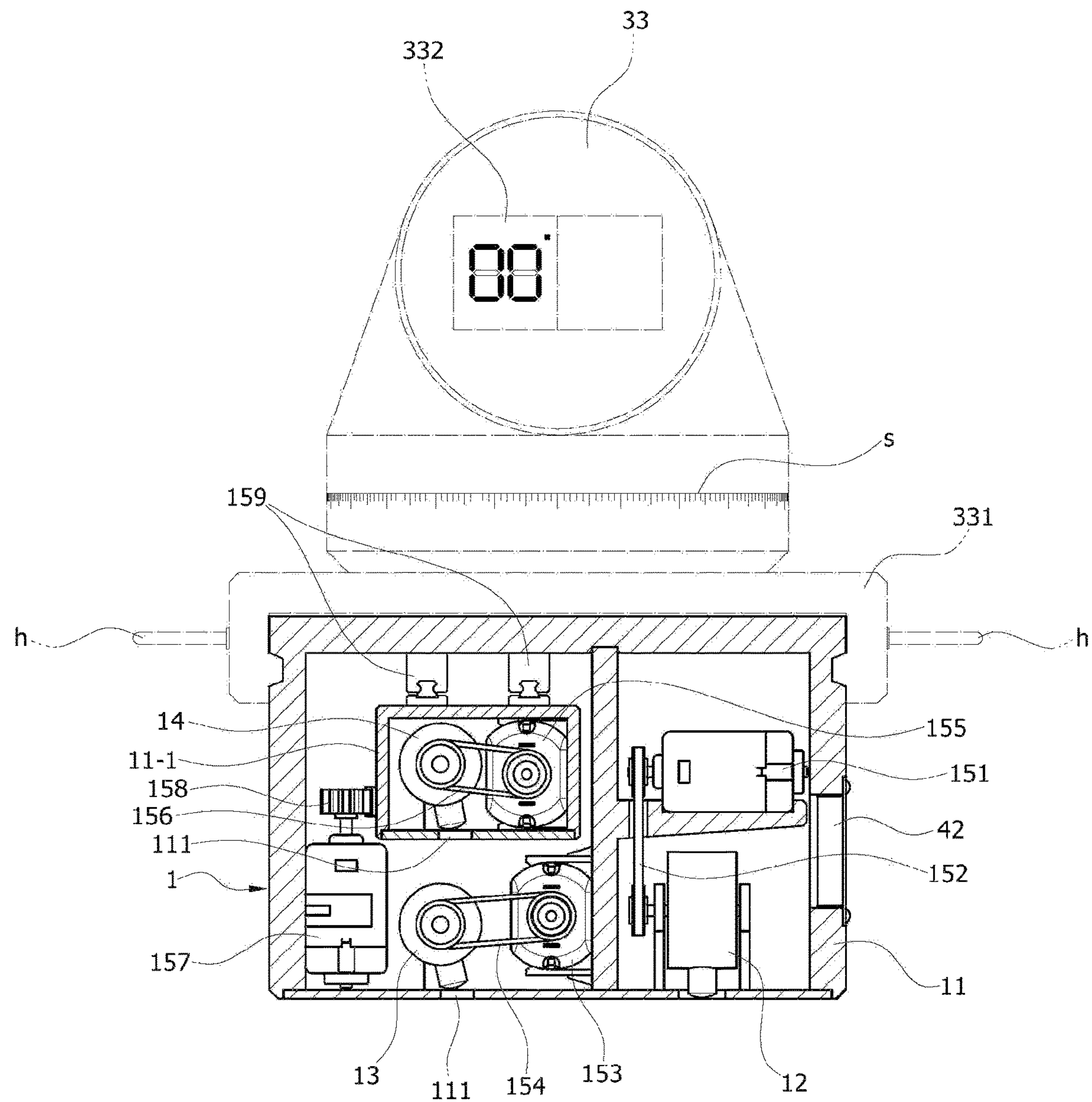

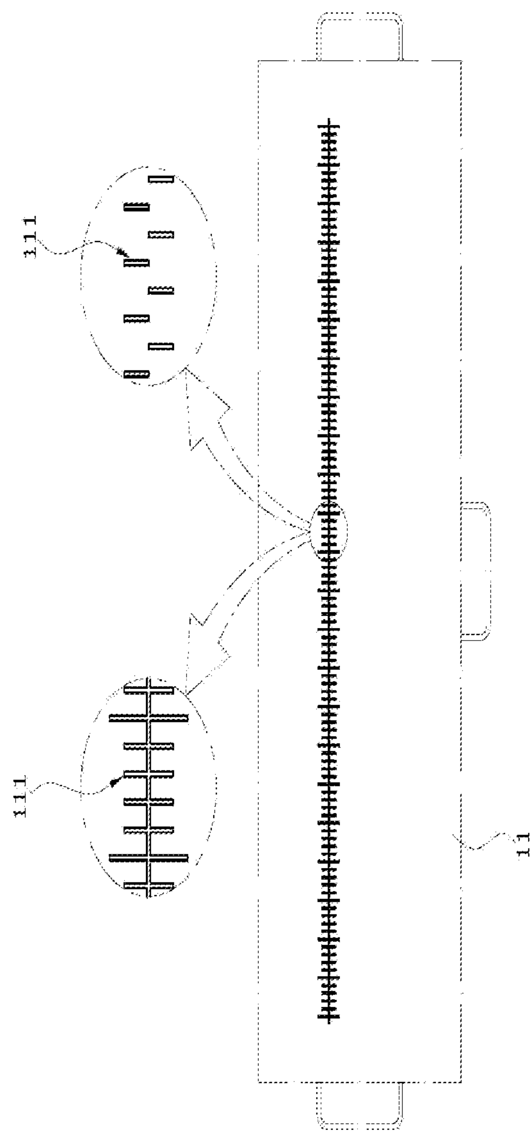
[FIG. 6]
111
111
11

[FIG. 7]
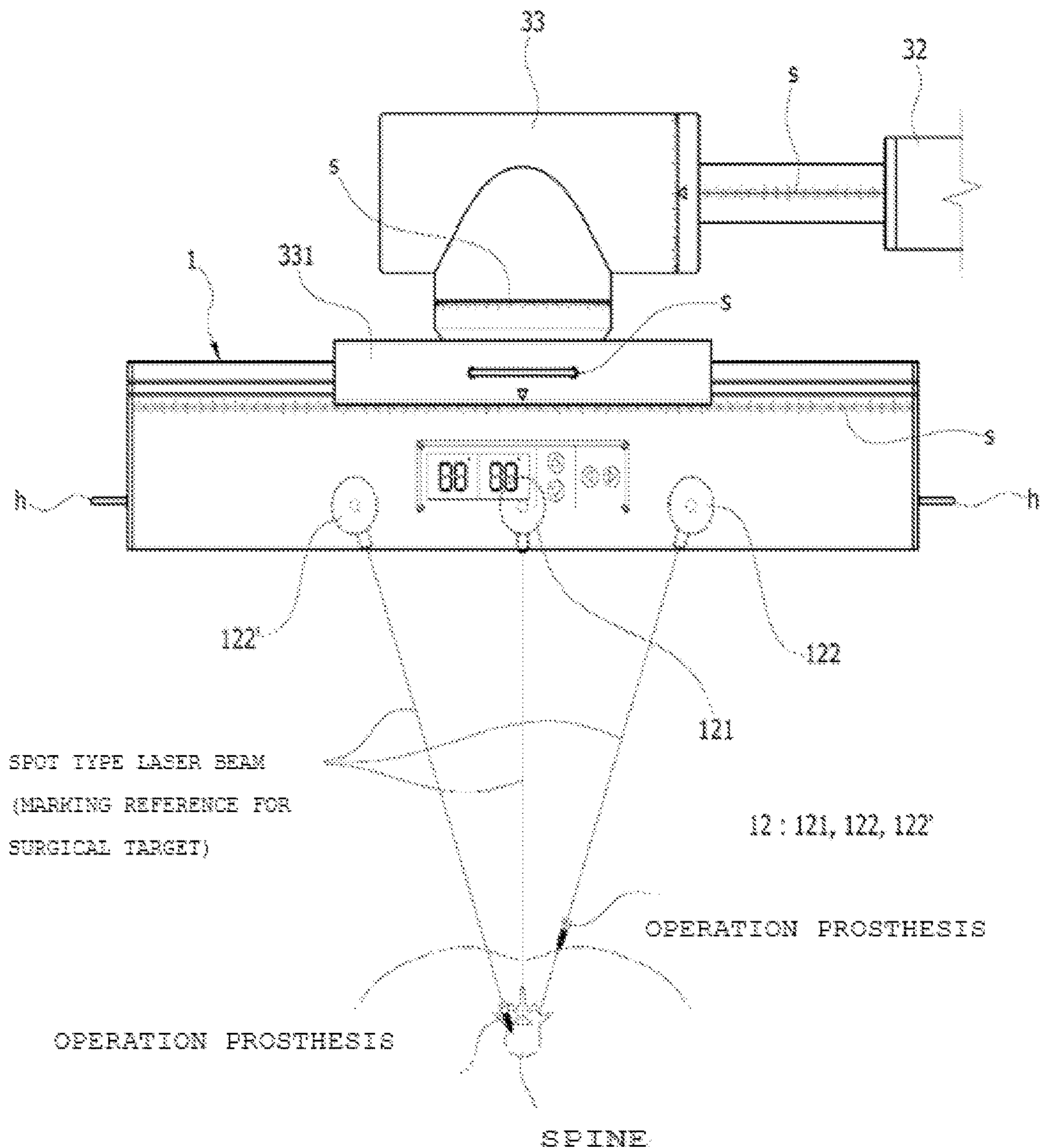

[FIG. 8]
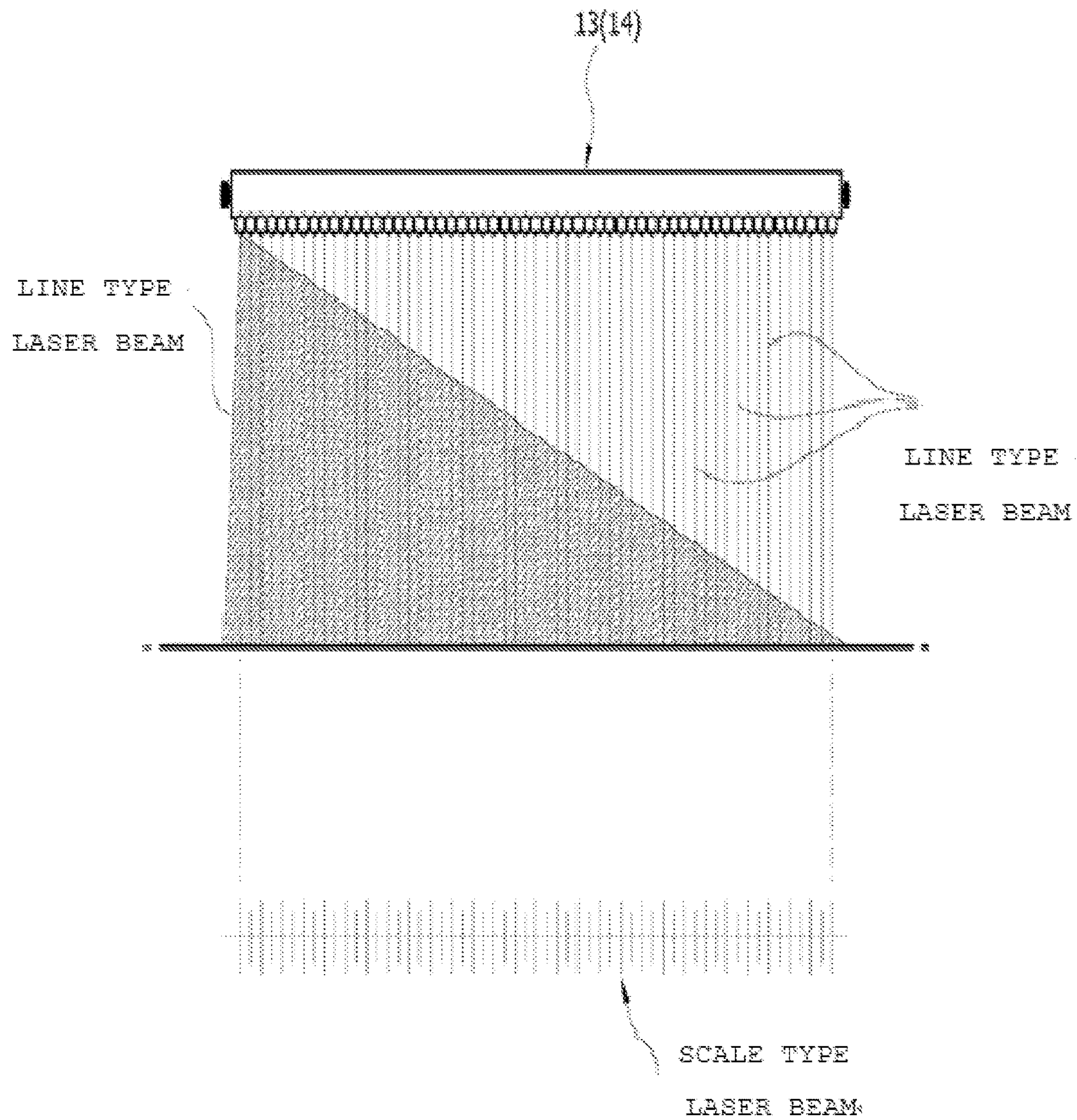

[FIG. 9]
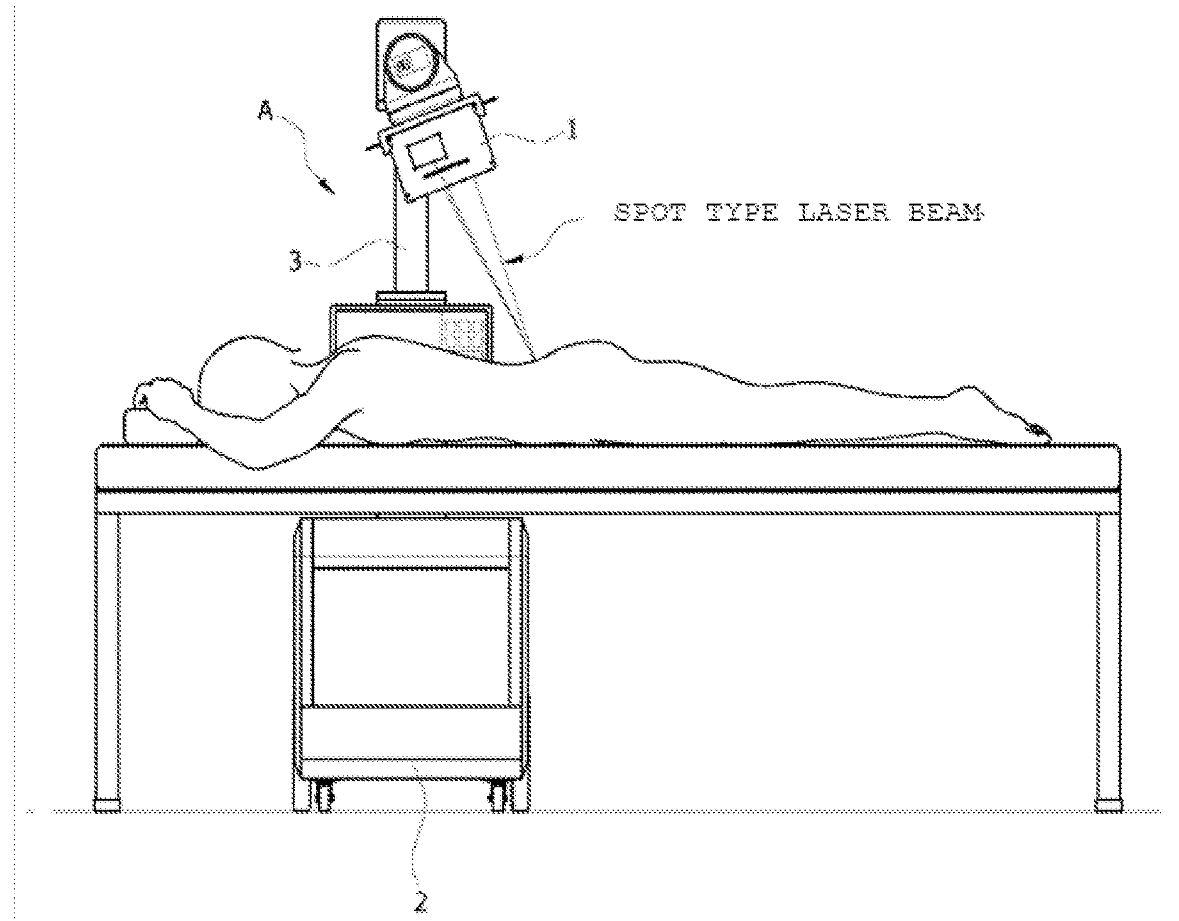

[FIG. 10(a)]
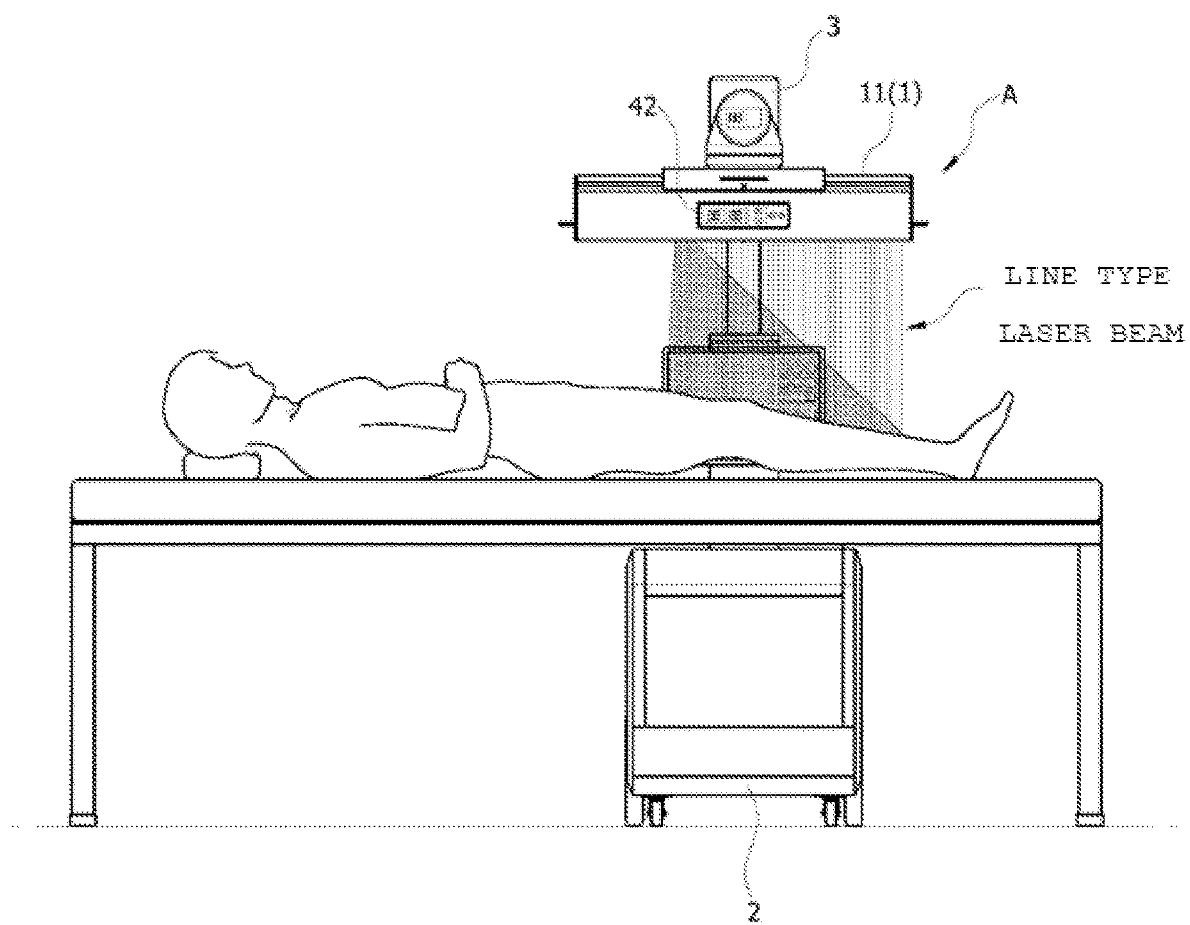

[FIG. 10(b)]
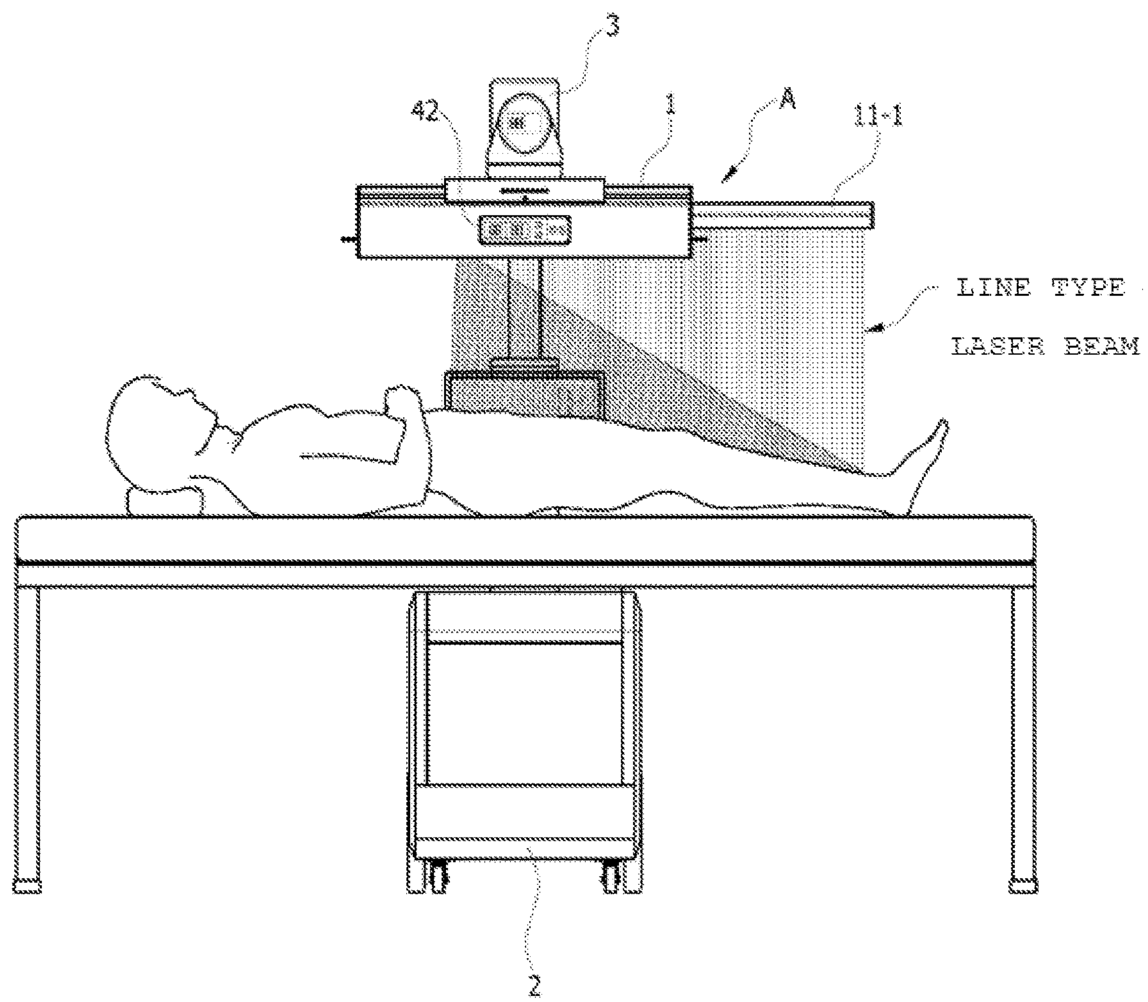

[FIG. 11(a)]
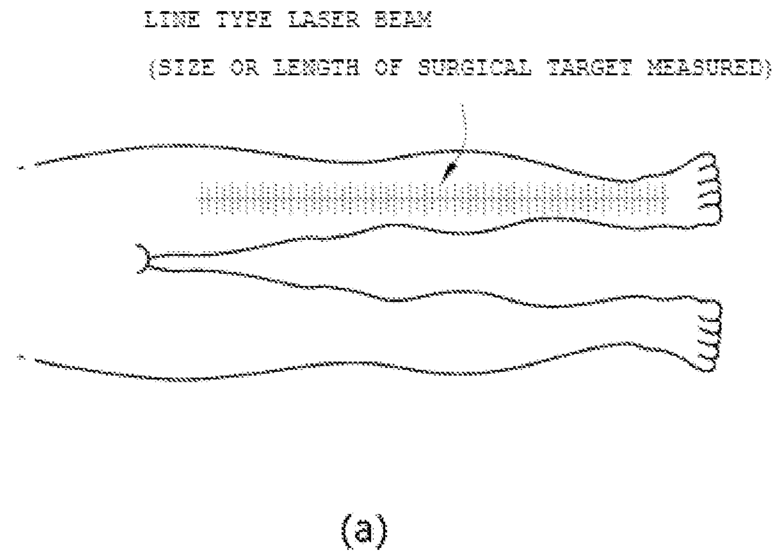
(a)
[FIG. 11(b)]
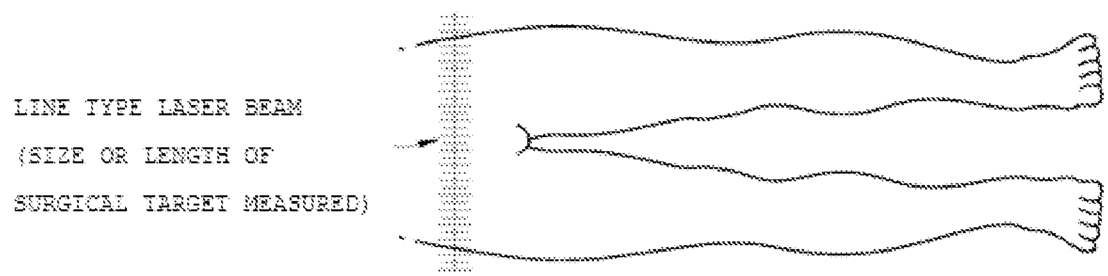
(b)

MULTIPURPOSE LASER POINTING-EQUIPMENT FOR MEDICAL USE

CROSS-REFERENCE TO RELATED APPLICATIONS

This application is a continuation of Application No. PCT/KR2020/019167, filed on Dec. 27, 2020, which in turn claims the benefit of Korean Patent Application No. 10-2020-0002802, filed on Jan. 8, 2020, the disclosures of which are incorporated by reference into the present application.

TECHNICAL FIELD

The present disclosure relates to a multipurpose laser pointing-equipment for medical use, and more particularly to a multipurpose laser pointing-equipment for medical use that can minimize errors in an operation (treatment, surgery) by definitely marking a reference (point, angle) for a surgery part from the outside the patient's body using point and line types of laser beams and by making it possible to accurately measure the surgical target.

BACKGROUND ART

The medical diagnosis field that has used only X-ray film since discovery of X-rays by Wilhelm Conrad Roentgen brought digital radiography (DR) with scientific development, and is developing diagnosis image devices and changing into a digital type using the DR.

Considering these development and change go along the lines of development of the IT industry, construction of a digital environment for the medical diagnosis field is recognized as a future-oriented project of medical images and new medical equipment and a corresponding medical software technology are being developed incredibly fast. Further, it is considered as necessary conditions to apply and use the information technology throughout the medical field.

However, in spite of such development of medical equipment and medical software described above, the medical field still highly depends on people (operators), so medical accidents or medical errors keep occurring.

For example, when a screw passes through the inside or the outside of a superior vertebral notch due to an inappropriate direction while the screw is inserted into the superior vertebral notch in spondylosyndesis, it exerts a harmful influence on the operation result such as causing neurological injury.

For this reason, the pedicle screw insertion angle is determined before an operation using X-ray, C-arm fluoroscopy, CT, and MRI for more accurate pedicle screw insertion. Nevertheless, the examples of wrong screw insertion are as small as 8% and as large as 40%, depending on operators.

Accordingly, a vertebral navigation system that is applied to pedicle screw insertion has been developed to minimize exposure to radiation and enables a more accurate operation. However, it is difficult to determine the position of a screw in real time due to a position change, etc. by external force when using CT (computer tomography) images taken before an operation or a C-arm, so examples of wrong screw insertion are reported.

Further, when C-arm fluoroscopy is used, since an object (examination part) is positioned between a radiation tube and a detector, as the distance from the detector or the center point increases, enlargement and errors are unavoidable due to the characteristics of X-rays that are radially radiated unlike an X-ray apparatus that takes images with an object in close contact with a detector.

Further, most measurement is possible before treating a patient due to digitization of medical images, so a treatment plan is made on the basis of medical images, but errors are unavoidably generated when the plan is actually applied. Further, since most operators depend on their proficiency rather than effectively using devices and uses in actual treatment, there are large differences in safety and accuracy. Furthermore, even skilled operators cannot easily approach target parts without opening the surgical target because the structures of the parts that are not visible in the bodies of patients are different, depending on the positions.

In order to solve this problem, a position guidance apparatus for a backbone operation that can safely insert a screw into an extra gap between a connecting portion of a transverse process and a vertebral body and the outer side of a pedicle without checking the insertion position of the screw using expensive medical equipment and that removes the need for checking whether injury of a nerve bundle even after insertion has been disclosed in Korean Utility Model No. 20-0198708.

FIG. 1 is a use state view showing a backbone operation using a position guidance apparatus for a backbone operation according to the related art. The position guidance apparatus 900 for a backbone operation, as shown in FIG. 1, includes: a position guide unit 907 composed of a hollow positioner 908, a hollow guider 910 disposed in parallel with the positioner 908 through a connecting portion 909, and a position rod 908' inserted in the positioner 908 to move up and down; and an angle controller 912 controlling angle of the position guide unit 907, in which the position controller 912 includes: a fixing bar 923 being fixed to an olecranon process 902 of a pedicle 901 and having a handle **913*a* for determining a reference position; an arc-shaped protractor 914 having a fine angle scale to show a controlled angle of the position guide unit 907 with respect to the fixing bar 913; and a fixing unit 915 for fixing the positioner 908 of the position guide unit 907 and the fixing bar 913 to the protractor 914** at a controlled angle.

According to the related art, the fixing bar 913 of the angle controller 912 is fixed to the olecranon process 902 of the pedicle 901, the positioner 908 of the position guide unit 907 is moved a predetermined angle by loosening the fixing unit 915 fixing the position guide unit 907 to the protractor 914, the movement angle is checked on the basis of the scale on the protractor 914, and then the position guide unit 907 is fixed again to the protractor 914 by the fixing unit 915.

Next, the position rod 908' inserted in the positioner 908 is moved to be positioned between a transverse process 903 of the pedicle 901 and a rib, whereby not only contact with the rib is prevented by a first anti-interference angle $\alpha$ and a second anti-interference angle $\beta$ of a first curved portion and a second curved portion of the position rod 908', it is possible to know the position of an outer wall 'a' at which the second curved portion is positioned from anatomical data in the medical field without specific experiences or knowledge.

That is, not only it is not required to use expensive medical equipment to check accuracy at every moment during a surgery, but a screw, which is inserted into a pedicle diameter (D) that is an extra gap between the outer wall 'a' connecting the transverse process 903 and the vertebral body and the outer side of the pedicle 901, is positioned as close as possible to the transverse process 903 and the outer wall 'a' of the vertebral body, so there is an effect that it is not required to check whether spinal nerves are injured even after inserting the screw.

However, since the entire process of the operation (surgery) described above is performed manually by operators, the degree of dependency on operators are unavoidably high, so even very skilled operators cannot avoid errors and may injure unnecessary parts. Accordingly, the problems described above still unavoidably remain.

A medical navigation system that finds out the current positions of surgical instruments using trackers attached to a patient and the surgical instruments and that is equipped with a navigator that uses 3D scanning for showing the positions of surgical instruments in images of the inside of a human body displayed on a monitor using image information taken in advance through computed tomography and MRI systems to be able to find out a surgical position has been disclosed in Korean Patent No. 10-2056436. However, this system has a problem with compatibility with other medical equipment, requires experts for handling the system, and has a problem of delay of diagnosis and an operation due to the performance characteristic of the system.

Further, this system has several problems, for example, a navigation surgery is difficult to stop once started, is difficult to be applied to simple operations, and is difficult for small and middle-sized hospitals to purchase it because it is expensive medical equipment.

As a result, it is highly required to develop a medical multipurpose pointing device that can mark a reference (level marking) of a surgical target from the outside of a patient in a non-contact type minimizing contamination and that makes it possible to measure (measure size and length and obtain information) of various diseased parts, organs, tissues, or the like.

PRIOR ART DOCUMENT

Patent Document (Patent Document 1) (Document 1) Korean Utility Model No. 20-0198708 (registered 2000.07.25)

(Patent Document 2) (Document 2) Korean Utility Model No. 20-0364087 (registered 2004.09.30)

(Patent Document 3) (Document 3) Korean Patent No. 10-2056436 (registered 2019.12.10)

DISCLOSURE

Technical Problem

In order to solve the problems described above, an objective of the present disclosure is to provide multipurpose laser pointing-equipment for medical use that more accurately marks a reference for a surgical target in a non-contact type from the outside of a patient's body using a laser point which emits a laser beam in a point or line type to the surgical target, and that enables more definite and various positioning before an operation (treatment, surgery) such as measuring not only an insertion angle of an operation instrument, an implant, a prosthesis, or the like into the surgical target, but the size or length of the surgical target.

Technical Solution

In order to achieve the objectives, the present disclosure is characterized by including: a pointer assembly lifted from a floor and emitting downward a laser beam for marking a reference for a surgical part on the body of a patient and for measuring a surgical range; a standing base being a basis for supporting the equipment in an erect position; a positioning supporter being erect on the standing base to lift the pointer assembly and adjust a height, a position, and an angle of the pointer assembly; and a controller disposed at a position for a user to operate the equipment.

Further, the pointer assembly includes: an assembly housing being a main body of a combination of components; a guide pointer disposed in the assembly housing and emitting a laser beam for marking a reference for a surgical part; a first marking pointer further disposed in the assembly housing and emitting a laser beam for measuring a surgical range; a second marking pointer further disposed in the assembly housing and expanding a range of the laser beam emitted from the first marking pointer so that extension measurement of a surgical range is possible; and a driving unit for adjusting angles of the guide pointer and the first and second making pointers and a position of the second marking pointer.

The positioning supporter includes a vertical support maintaining an erect state from a top of the standing base, a horizontal support maintaining a horizontal state from an upper end of the vertical support, and a hinge head disposed at a front end of the horizontal support to adjust vertical and horizontal angles of the pointer assembly; and the vertical support and the horizontal support each have a stretchable structure to be able to adjust the height, the position, and the direction of the pointer assembly.

Further, the assembly housing further includes an extension rod longitudinally reciprocating from at least one side to adjust the position of the second marking pointer.

Further, the guide pointer includes a vertical pointer emitting a laser beam to a surgical target to indicate a center of the surgical target, and at least one or more angle pointers spaced apart from each other at both sides of the vertical pointer and emitting a laser beam to a surgical target to indicate an insertion angle of an operation instrument or an operation implant—a prosthesis; and the vertical pointer and the angle pointers are laser pointers emitting a laser beam in a spot shape onto an emission target.

Further, the first and second marking pointers are laser pointers that emit laser beams like a scale in a line, which makes it possible to measure a size and a length of a surgical target, onto an emission target.

Further, the hinge head has a structure that vertically rotates around a longitudinal direction and horizontally rotates around a vertical direction to be able to adjust emission angles of the laser beams emitted from the guide pointer and the first and second marking pointers; has a guide clamp disposed thereunder to enable the pointer assembly to be lifted and mounted and to longitudinally move in the mounted state; and has a digital protractor for showing an emission angle of the laser beam emitted from the pointer assembly when the hinge head vertically rotates around the longitudinal direction.

Further, marking holes through which the laser beams emitted from the guide pointer and the first and second marking pointer passes are formed through a bottom of the assembly housing and a bottom of the extension rod, and are formed like a scale of measurer so that a size and a length of a surgical target can be measured.

Further, the driving unit includes: a first driving motor and a first power transmission member that rotate the angle pointers in the assembly housing to adjust emission angles of the laser beams emitted from the angle pointers; a second driving motor and a second power transmission member that rotate the first marking pointer in the assembly housing to adjust an emission angle of the laser beam emitted from the first marking pointer; a third driving motor and a third power transmission member that rotate the second marking pointer in the extension rod to adjust an emission angle of the laser beam emitted from the second marking pointer; a fourth driving motor and a fourth power transmission member that reciprocate the extension rod longitudinally from at least one side in the assembly housing to adjust a position of the second marking point; and a guide member that guides reciprocation of the extension rod in cooperation with the assembly housing and the extension rod.

Advantageous Effects

As can be seen from the above description, according to the multipurpose laser pointing-equipment for medical use of the present disclosure, since the laser point (the guide pointer of the pointer assembly) that emits a laser beam in a point type indicates not only a reference for a surgical target, but the angles of an operation implant and a prosthesis, it is possible to insert an operation instrument or an operation implant and a prosthesis. Accordingly, there is an effect that it is possible to prevent factors that have bad influence on an operation result such as neurological injuries due to wrong insertion of an operation implant and prosthesis.

Further, since laser beams are emitted to a surgical target like the scale of a measurer by a combination of the laser pointers (the first marking pointers of the pointer assembly) that emit laser beams in a line type, it is possible to achieve an effect that it is possible to accurately measure the size or length of a part to be operated (a diseased part, an organ, a tissue, etc.). Further, it is possible to achieve an effect that it is possible to measure the size or length, which is difficult to measure using only the first marking pointer, by additionally using other laser pointers (the second marking pointer of the pointer assembly) that emit a laser beam in a line type.

Further, by achieving various effects described above, it is possible to compensate for and correct defects of automate medical equipment (a robot surgery, a navigation surgery), errors due to manual system (expertness of doctors), it is possible to reduce exposure by relatively decreasing use of medical radiation equipment, and it is possible to reduce a treatment time and minimize side effects due to wrong operations (treatment, surgery), thereby considerably contributing to improvement of the success ratio of treatment. Further, it is possible to increase accuracy of operation implant-prostheses insertion such as pedicle screw insertion and it is possible to apply the present disclosure to various other operations, so it is possible to satisfy the demands for safely receiving treatment of patients and correspondingly secure competitiveness of the product. Accordingly, the present disclosure is useful for profit creation and can remarkably contribute to developing and activating the medical industry.

DESCRIPTION OF DRAWINGS

FIG. 1 is a use state view showing a backbone operation using a position guidance apparatus for a backbone operation according to the related art;

FIG. 2 is a perspective view showing the configuration relationship of multipurpose laser pointing-equipment for medical use according to the present disclosure;

FIGS. 3(*a*) and 3(*b*) are exemplary operation views showing the relationship of the position and turning of a pointer assembly of the multipurpose laser pointing-equipment for medical use according to the present disclosure;

FIG. 4 is an exemplary operation view showing reciprocation of an extension rod of the pointer assembly of the multipurpose laser pointing-equipment for medical use according to the present disclosure;

FIG. 5 is a cross-sectional view of main parts showing the internal structure of the pointer assembly of the multipurpose laser pointing-equipment for medical use according to the present disclosure;

FIG. 6 is a use state view showing disposition and embodiment of a guide pointer of the pointer assembly of the multipurpose laser pointing-equipment for medical use according to the present disclosure;

FIG. 7 is an exemplary configuration view showing formation relationship of marking holes formed on the bottom of an assembly housing of the pointer assembly of the multipurpose laser pointing-equipment for medical use according to the present disclosure;

FIG. 8 is a use state view showing an embodiment of a first marking pointer of the pointer assembly of the multipurpose laser pointing-equipment for medical use according to the present disclosure; and FIG. 9, FIG. 10(*a*), FIG. 10(*b*), FIG. 11(*a*) and FIG. 11(*b*) are use state views showing embodiment relationship of the multipurpose laser pointing-equipment for medical use according to the present disclosure.

MODE FOR INVENTION

Hereafter, exemplary embodiments of the present disclosure are described in detail with reference to the accompanying drawings such that those skilled in the art can easily achieve the present disclosure.

It should be noted that when components are given reference numerals in the drawings, the same components are given the same reference numerals even if they are shown in different drawings. In describing the present disclosure, well-known functions or constructions will not be described in detail since they may unnecessarily obscure the understanding of the present disclosure.

In the accompanying drawings, FIG. 2 is a perspective view showing the configuration relationship of multipurpose laser pointing-equipment for medical use according to the present disclosure, FIGS. 3*a* and 3*b* are exemplary operation views showing the relationship of the position and turning of a pointer assembly of the multipurpose laser pointing-equipment for medical use according to the present disclosure, FIG. 4 is an exemplary operation view showing reciprocation of an extension rod of the pointer assembly of the multipurpose laser pointing-equipment for medical use according to the present disclosure, FIG. 5 is a cross-sectional view of main parts showing the internal structure of the pointer assembly of the multipurpose laser pointing-equipment for medical use according to the present disclosure, FIG. 6 is a use state view showing disposition and embodiment of a guide pointer of the pointer assembly of the multipurpose laser pointing-equipment for medical use according to the present disclosure, FIG. is an exemplary configuration view showing formation relationship of marking holes formed on the bottom of an assembly housing of the pointer assembly of the multipurpose laser pointing-equipment for medical use according to the present disclosure, and FIG. 8 is a use state view showing an embodiment of a first marking pointer of the pointer assembly of the multipurpose laser pointing-equipment for medical use according to the present disclosure.

As shown in FIGS. 2 to 4, multipurpose laser pointing-equipment for medical use A according to the present disclosure includes; a pointer assembly 1 lifted from a floor and emitting downward a laser beam for marking a reference for a surgical part on the body of a patient lying on a bed (medical bed) and for measuring a surgical range; a standing base 2 being a basis for supporting the equipment in an erect position; a positioning supporter 3 being erect on the standing base 2 to lift the pointer assembly 1 and adjust the height, position, and angle of the pointer assembly 1; and a controller 4 disposed at a position for a user to operate the equipment.

The pointer assembly 1 is provided to emit a laser beam for marking a reference for a surgical target such as a surgical point and a surgical angle and measuring a surgical range such as the size or the length of a diseased part or an organ to a patient. As shown in FIG. 5, the pointer assembly 1 includes; an assembly housing 11 that is a main body of a combination of components; a guide pointer 12 disposed in the assembly housing 11 and emitting a laser beam for marking a reference for a surgical part; a first marking pointer 13 further disposed in the assembly housing 11 and emitting a laser beam for measuring a surgical range; a second marking pointer 14 further disposed in the assembly housing 11 and expanding the range of the laser beam emitted from the first marking pointer 13 so that extension measurement of a surgical range is possible; and a driving unit 15 for adjusting the angles of the guide pointer 12 and the first and second making pointers 13 and 14 and the position of the second marking pointer 14.

The assembly housing 11 further includes an extension rod 11-1 that longitudinally reciprocates from at least one side to adjust the position of the second marking pointer 13 (see FIGS. 2 and 4).

Marking holes 111 through which the laser beams emitted from the guide pointer 12 and the first and second marking pointers 13 passes are formed through the bottom of the assembly housing 11 and the bottom of the extension rod 11-1, and, as shown in FIG. 6, are preferably formed like scales of various patterns (e.g., a cross, a lattice, etc.) so that the size and the length of a surgical target can be measured.

The guide pointer 12, as shown in FIG. 7, includes a vertical pointer 121 that emits a laser beam to a surgical target to indicate the center of the surgical target, and at least one or more angle pointers 122 and 122' that are spaced apart from each other at both sides of the vertical pointer 121 and emit a laser beam to a surgical target to indicate the insertion angle of an operation instrument or an operation implant—a prosthesis (a pedicle screw, etc.).

The vertical pointer 121 and the angle pointers 122 and 122', which are laser pointers emitting a laser beam in a spot shape onto an emission target, can function as indicators having various functions by emitting laser beams with several colors and wavelengths.

The first and second marking pointers 13 and 14, as shown in FIG. 8, are laser pointers that emit laser beams like a scale in a line, which makes it possible to measure the size and the length of a surgical target, onto an emission target. Several first and second marking pointers 13 and 14 are disposed at predetermined positions to emit laser beams like the scale of a measurer and can function as indicators that have various functions by emitting laser beams with various colors and wavelength, similar to the guide pointer 12.

The driving unit 15, as shown in FIG. 5, includes: a first driving motor 151 and a first power transmission member 152 that rotate the angle pointers 122 and 122' of the guide pointer 12 in the assembly housing 31 to adjust the emission angles of the laser beams emitted from the angle pointers 122 and 122'; a second driving motor 153 and a second power transmission member 154 that rotate the first marking pointer 13 in the assembly housing 31 to adjust the emission angle of the laser beam emitted from the first marking pointer 13; a third driving motor 155 and a third power transmission member 156 that rotate the second marking pointer 14 in the extension rod 11-1 to adjust the emission angle of the laser beam emitted from the second marking pointer 14; a fourth driving motor 157 and a fourth power transmission member 158 that reciprocate the extension rod 11-1 in the assembly housing 11; and a guide member 159 that guides reciprocation of the extension rod 11-1 in cooperation with the assembly housing 11 and the extension rod 11-1.

The first, second, third, and fourth driving motors 151, 153, 155, and 157 are preferably stepping motors that rotate an angle proportioned to a given number of pulses because they give orders to pulses in step states in consideration of precise angle adjustment of the angle pointers 122 and 122' and the first and second marking pointers 13 and 14 and precise reciprocation of the extension rod 11-1, but they are not necessarily limited thereto and any mechanical element may be employed as long as it performs the same operation.

The first, second, and third power transmission members 152, 154, and 156 are preferably pulley-and-belts that transmit power generated by the first, second, and third driving motors 151, 153, and 155 to the angle pointers 122 and 122' and the first and second marking pointers 13 and 14, but they are not necessarily limited thereto and any mechanical element may be employed as long as it shows the same operation effect.

The fourth power transmission member 158 is preferably a rack-and-pinion that transmits power generated by the fourth driving motor 157 to the extension rod 11-1 and converts a rotation motion into a straight motion, but it is not necessarily limited thereto and any mechanical element may be employed as long as it shows the same operation effect.

The guide member 159 is preferably a slide rail that guides reciprocation of the extension rod 11-1 by the fourth power transmission member 158, but it is not necessarily limited thereto and any mechanical element may be employed as long as it shows the same operation effect.

The standing base 2, which is provided to keep the positioning supporter 3 erected and the pointer assembly 1 lifted by the positioning supporter 3, is preferably a weight that applies predetermined load, and as shown in FIGS. 2 to 4, is preferably equipped with a caster 21 in consideration of convenience of movement.

The positioning supporter 3, which is provided to lift the pointer assembly 1 and adjust the position of the pointer assembly 1, as shown in FIGS. 2 and 3*a*, includes a vertical support 31 that maintains an erect state from the top of the standing base 2, a horizontal support 32 that maintains a horizontal state from the upper end of the vertical support 31, and a hinge head 33 that is disposed at the front end of the horizontal support 32 to adjust the vertical and horizontal angles of the pointer assembly 1.

It is preferable that the vertical support 31 and the horizontal support 32 each have a stretchable structure to be able to adjust the height, position, and direction of the pointer assembly 1.

It is preferable that the hinge head 33 has a structure that vertically rotates around the longitudinal (horizontal) direction and horizontally rotates around the vertical direction to be able to adjust the emission angles of the laser beams emitted from the guide pointer 12 and the first and second marking pointers 13 and 14. A guide clamp 331 that enables the pointer assembly 1 to be lifted and mounted and to longitudinally move in the mounted state is disposed under the hinge head, and a digital protractor 332 for showing the emission angle of the laser beam emitted from the pointer assembly 1 when the hinge head vertically rotates around the longitudinal direction is provided.

The controller 4, which is provided for a user to operate the equipment including the operation of the pointer assembly 1 in addition to turning on/off the power, as shown in FIGS. 2 and 4, includes a main controller 41 for operating the entire equipment and a sub-controller 42 disposed at the pointer assembly 1 to operate the pointer assembly 1.

The main controller 41, which is provided for a user to operate the entire equipment, is preferably include several operation buttons for inputting and setting programs for driving the equipment, and a display that displays driving information.

The sub-controller 42, which is provided for directly operating the pointer assembly 1, preferably includes operation buttons for movement and angle adjustment of the assembly housing 11 and reciprocation of the extension rod 11-1, and a display that displays information about the movement and angle adjustment.

Reference numeral 'a' not stated above indicates an operation handle for a user to manually move the pointer assembly and adjust the angle of the pointer assembly, and reference numeral 's' indicates scales marked at predetermined portions of the vertical support and the horizontal support of the positioning supporter, and the assembly housing and the extension rod of the pointer assembly to check not only the height, but the position, the angle, and the operation of the pointer assembly.

The operation of the multipurpose laser pointing-equipment for medical use A having the above configuration according to the present disclosure is described in detail hereafter.

FIGS. 9 to 11 (*a*) and (*b*) are use state views showing embodiment relationship of the multipurpose laser pointing-equipment for medical use according to the present disclosure. As shown in FIG. 9, the multipurpose laser pointing-equipment for medical use A of the present disclosure is used to mark a reference for a surgical target before an operation (treatment, surgery), and to measure a surgical target, as shown in FIGS. 10*a* to 11(*a*) and (*b*).

For example, when spin instabilities such as spondylolysis, spondylolisthesis, and retrolisthesis accompany or spin instabilities are expected, spinal fusion (spinal fixation) that makes bony ankylosis by fusing two or more spines so that the spines cannot be moved is generally applied. Spine fusion is a surgery of inserting pedicle screws into a pedicle and stably fixing two or spines by connecting the screws.

It is possible to prevent factors that have bad influence later on an operation result such as neurological injuries due to wrong insertion of screws in spine fusion only when a process of accurately marking a reference for a surgical target should be performed before spine fusion described above, and the multipurpose laser pointing-equipment for medical use A of the present disclosure is used for this purpose.

In detail, as shown in FIG. 9*a*, a reference is marked on a surgical target of the body of a patient lying on a medical bed, in which the equipment is moved to an appropriate position by moving the standing base 2 and then the equipment is started by operating the main controller 41 of the controller 4. In this case, it is convenient to move the equipment because a caster 'c' is mounted under the standing base 2.

Next, the lengths of the vertical support 31 and the horizontal support 32 of the positioning supporter 3 are adjusted by operating again the main controller 41, whereby the pointer assembly 1 is moved to a predetermined position. In this state, a laser beam is emitted from the pointer assembly 1 to travel to the surgical target.

Next, the hinge head 33 of the positioning supporter 3 is vertically rotated around the longitudinal direction by operating the sub-controller 42 of the controller 4 disposed at the pointer assembly 1, whereby the angle of the pointer assembly 1 is adjusted and the pointer assembly 1 is moved to a desired position. Further, the vertical pointer 121 of the guide pointer 12 disposed in the assembly housing 11 of the pointer assembly 1 vertically emits a laser beam accurately to the surgical target.

Next, the sub-controller 42 is operated again such that the angle of at least one of the angle pointers 122 and 122' of the guide pointer 12 by the first driving motor 151 and the first power transmission member 152 of the driving unit 15 of the pointer assembly 1, whereby the insertion angle of a operation instrument or screws that are operation prostheses to be inserted into the surgical target are shown and indicated (see FIG. 6) by the laser beams emitted from the angle pointers 122 and 122' to the surgical target. Accordingly, an operator can more accurately and precisely insert the operation prostheses.

Meanwhile, it is possible to measure the position of a point (surgical target), into which pedicle screws are inserted, from a specific part of a patient's body in spinal fixation or to measure the length, etc. of a diseased part or an organ in other operations using the first marking pointer 13 of the pointer assembly 1. In detail, this is possible by operating the sub-controller 42 to emit a laser beam with the angle of the first marking pointer 13 adjusted.

In this case, since the first marking pointer 13 includes a combination of several laser pointers, laser beams can be emitted like the scale of a measurer onto the surgical target (see FIGS. 8, 10*a*, and 11(*a*) and (*b*)), and accordingly, the surgical target can be measured.

When it is impossible to measure the size or length of the surgical target using only the first marking pointer 13, it is possible to extend the measurement range of the surgical target using the second marking pointer 14. That is, the fourth driving motor 157 and the fourth power transmission member 158 of the driving unit 15 are operated by operating the sub-controller 42 such that the extension rod 11-1 protrudes to the outside while being guided by the guide member 159 from at least one side of the assembly housing 11, whereby, as shown in FIG. 10, the second marking pointer 14 disposed in the extension rod 11-1 is moved and a laser beam can be emitted from an extension line of the first making pointer 13 to travel to the part of the body.

It is possible to know the protruding range of the extension rod 11-1 through an angle display window of the sub-controller 42.

Meanwhile, in addition to the electric operation of the equipment described above, a user can manually move the pointer assembly 1, which can be achieved using the handles 'h' disposed on the assembly housing 11 and the guide clamp 331 of the hinge head 33.

In short, according to the multipurpose laser pointing-equipment for medical use A of the present disclosure, since the guide pointer 12 of the pointer assembly 1 that emits a laser beam in a point type indicates not only a reference for a surgical target, but the angles of an operation implant—a prosthesis, it is possible to insert an operation instrument or an operation implant—a prosthesis. Accordingly, it is possible to achieve an effect that it is possible to prevent factors that have bad influence on an operation result such as neurological injuries due to wrong insertion of an operation implant-prosthesis.

Further, since laser beams are emitted to a surgical target like the scale of a measurer by a combination of the first marking pointers 13 of the pointer assembly 1 that emit laser beams in a line type, it is possible to achieve an effect that it is possible to accurately measure the size or length of a part to be operated (a diseased part, an organ, a tissue, etc.). Further, it is possible to achieve an effect that it is possible to measure the size or length, which is difficult to measure using only the first marking pointer 13, by additionally using the second marking pointer 14 of the pointer assembly 1 that emits a laser beam in a line type.

The above description merely explains the spirit of the present disclosure and the present disclosure may be changed, modified, and replaced in various ways without departing from the spirit of the present disclosure by those skilled in the art. Accordingly, the embodiments described herein and the accompanying drawings are provided merely not to limit, but to explain the spirit of the present disclosure, and the spirit of the present disclosure is not limited by the embodiments and the accompanying drawings. The patent right of the present disclosure should be construed by the following claims and the scope and spirit of the disclosure should be construed as being included in the patent right of the present disclosure.

REFERENCE NUMERALS

| | |
|---|---|
| A: | pointing equipmnet |
| 1: | pointer assembly |
| 2: | standing base |
| 3: | positioning supporter |
| 4: | controller |
| 11: | assembly housing |
| 11-1: | extension rod |
| 12: | guide pointer |
| 13: | first marking pointer |
| 14: | second marking pointer |
| 15: | driving unit |
| 21: | caster |
| 31: | vertical support |
| 32: | horizontal support |
| 33: | hinge head |
| 41: | mai controller |
| 42: | sub-controller |
| 111: | marking hole |
| 121: | vertical pointer |
| 122, 122': | angle pointer |
| 151: | first driving motor |
| 152: | first power transmission member |
| 153: | second driving motor |
| 154: | second power transmission member |
| 155: | third driving motor |
| 156: | third power transmission member |
| 157: | fourth driving motor |
| 158: | fourthpower transmissio member |
| 159: | guide member |
| 331: | rotary base |
| 332: | guide clamp |
| 332: | digital protractor |

The invention claimed is:

1. A multipurpose laser pointing-equipment for medical use comprising:

a pointer assembly lifted from a floor and emitting downward a laser beam for marking a reference for a surgical part on the body of a patient and for measuring a surgical range;

a standing base being a basis for supporting the equipment in an erect position;

a positioning supporter being erect on the standing base to lift the pointer assembly and adjust a height, a position, and an angle of the pointer assembly; and a controller disposed at a position for a user to operate the equipment, wherein, the pointer assembly includes:

an assembly housing being a main body of a combination of components;

a guide pointer disposed in the assembly housing and emitting a laser beam for marking a reference for a surgical part;

a first marking pointer disposed in the assembly housing and emitting a first laser beam for measuring the surgical range;

a second marking pointer disposed in the assembly housing emitting a second laser beam adjacent the first laser beam for increasing the surgical range; and a driving unit for adjusting angles of the guide pointer, adjusting angles of the first and second marking pointers, and adjusting a position of the second marking pointer, the assembly housing further comprises an extension rod longitudinally reciprocating from at least one side to adjust the position of the second marking pointer;

the guide pointer comprises:

a vertical pointer emitting a laser beam to the surgical target to indicate a center of the surgical target, and at least one or more angle pointers spaced apart from each other at both sides of the vertical pointer and emitting a laser beam to the surgical target to indicate an insertion angle of an operation instrument or an operation implant prosthesis; and the vertical pointer and the angle pointers are laser pointers emitting a laser beam in a spot shape onto an emission target, and the driving unit comprises:

a first driving motor and a first power transmission member that rotate the angle pointers in the assembly housing to adjust emission angles of the laser beams emitted from the angle pointers;

a second driving motor and a second power transmission member that rotate the first marking pointer in the assembly housing to adjust an emission angle of the laser beam emitted from the first marking pointer;

a third driving motor and a third power transmission member that rotate the second marking pointer in the extension rod to adjust an emission angle of the laser beam emitted from the second marking pointer;

a fourth driving motor and a fourth power transmission member that reciprocate the extension rod longitudinally from at least one side in the assembly housing to adjust a position of the second marking pointer; and a guide member that guides reciprocation of the extension rod in cooperation with the assembly housing and the extension rod.

2. The multipurpose laser pointing-equipment for medical use of claim 1, wherein the positioning supporter comprises:

a vertical support maintaining an erect state from a top of the standing base, a horizontal support maintaining a horizontal state from an upper end of the vertical support, and a hinge head disposed at a front end of the horizontal support to adjust vertical and horizontal angles of the pointer assembly; and the vertical support and the horizontal support each have a stretchable structure to be able to adjust the height, the position, and the direction of the pointer assembly.

3. The multipurpose laser pointing-equipment for medical use of claim 2, wherein the hinge head comprises:

an adjusting structure that vertically rotates around a longitudinal direction and horizontally rotates around a vertical direction to be able to adjust emission angles of the laser beams emitted from the guide pointer and the first and second marking pointers;

a guide clamp disposed thereunder to enable the pointer assembly to be lifted and mounted and to longitudinally move in the mounted state; and a digital protractor for showing an emission angle of the laser beam emitted from the pointer assembly when the hinge head vertically rotates around the longitudinal direction.

4. The multipurpose laser pointing-equipment for medical use of claim 1, wherein the first and second marking pointers are laser pointers configured to emit laser beams onto an emission target to allow for a size and a length of the surgical target to be measured.

5. The multipurpose laser pointing-equipment for medical use of claim 1, wherein marking holes, through which the laser beams emitted from the guide pointer and the first and second marking pointers pass, are formed through a bottom of the assembly housing and a bottom of the extension rod, such that a size and a length of the surgical target can be measured.

* * * * *